United States Patent [19]

Kanne et al.

[11] Patent Number: 5,215,998

[45] Date of Patent: Jun. 1, 1993

[54] ALKYLPHOSPHONOTHIOATE INSECTICIDES

[75] Inventors: David B. Kanne, Corte Madera; Charles G. Chavdarian, San Ramon, both of Calif.

[73] Assignee: Imperial Chemical Industries PLC, London, England

[21] Appl. No.: 629,536

[22] Filed: Dec. 18, 1990

[51] Int. Cl.$^5$ .............. A61K 31/44; A61K 31/47; C07D 215/00; C07D 213/02
[52] U.S. Cl. .................. 514/311; 514/315; 514/345; 514/357; 546/154; 546/155; 546/162; 546/242; 546/290; 546/296; 546/300; 546/301; 546/339; 546/345
[58] Field of Search .............. 546/154, 155, 162, 242, 546/290, 296, 300, 301, 339, 345; 514/311, 315, 345, 357

[56] References Cited

U.S. PATENT DOCUMENTS

| | | | |
|---|---|---|---|
| 3,118,889 | 1/1964 | Schroeder | 544/242 |
| 3,209,020 | 9/1965 | Schrader | 558/193 |
| 3,284,455 | 11/1966 | Fest et al. | 546/23 |
| 3,371,095 | 2/1968 | Lorenz et al. | 546/22 |
| 4,565,809 | 1/1986 | Chavdarian et al. | 514/112 |
| 4,567,168 | 1/1986 | Krüger et al. | 549/221 |
| 4,652,302 | 3/1987 | Gray et al. | 71/87 |
| 4,683,225 | 7/1987 | Chavdarian | 514/128 |

FOREIGN PATENT DOCUMENTS 1211647 3/1966 Fed. Rep. of Germany .
518979 1/1983 Spain .

Primary Examiner—Robert T. Bond
Assistant Examiner—Y. N. Gupta
Attorney, Agent, or Firm—Lynn Marcus-Wyner

[57] ABSTRACT

Compounds and compositions containing alkylphosphonothioates, for insecticidal control, particularly for use as soil and/or foliar insecticides, having the formula.

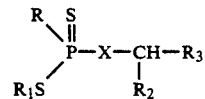

in which
R is $C_1-C_3$ alkyl;
$R_1$ is $C_4-C_6$ branched alkyl;
$R_2$ is hydrogen, methyl, ethyl, cyano or $C_2-C_4$ alkynyl;

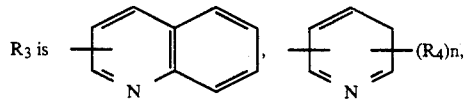

$R_4$ is halo, $C_1-C_2$ haloalkyl, $C_1-C_4$ alkoxy, $C_1-C_4$ thioalkyl or mono-or di-$C_1-C_2$ alkylamino;
n is 1-3; and
X is O or S.

18 Claims, No Drawings

ALKYLPHOSPHONOTHIOATE INSECTICIDES

SUMMARY OF THE INVENTION

This invention relates to a series of alkylphosphonothioate insecticides having the formula

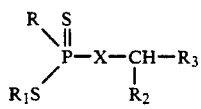

in which

R is $C_1$-$C_3$ alkyl;

$R_1$ is $C_4$-$C_6$ branched alkyl;

$R_2$ is hydrogen, methyl, ethyl, cyano or $C_2$-$C_4$ alkynyl;

$R_3$ is

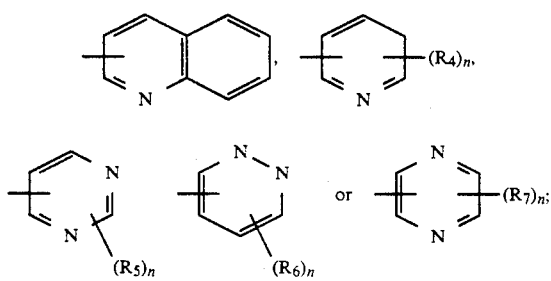

$R_4$ is halo, $C_1$-$C_4$ alkyl, $C_1$-$C_2$ haloalkyl, $C_1$-$C_4$ alkoxy, $C_1$-$C_4$ thioalkyl or mono-or di-$C_1$-$C_2$ alkylamino;

$R_5$, $R_6$ and $R_7$ are independently hydrogen, halo or $C_1$-$C_4$ alkyl;

n is 0-3; and

X is O or S;

together with insecticidal compositions containing such compounds, and methods of controlling insects.

The term "halo" includes chloro, bromo, fluoro and iodo, with chloro, bromo and fluoro being preferred. R is preferably methyl or ethyl. $R_1$ is preferably secondary or tertiary butyl. $R_2$ is preferably hydrogen. The substituents on the pyridine ring may be located at one or more of the four possible positions. Preferably n is 0, 1 or 2. $R_4$ preferably is methyl, halo or haloalkyl.

The term "insects" as used herein refers to the broad and commonly understood usage rather than to those small invertebrate animals which in the strict biological sense are classified as insects, and includes in addition to those belonging to the class Insecta, some classes of acarids such as spiders, mites, ticks and the like, particularly mites.

The compounds of the present invention may be prepared by two general methods. Method A is used to prepare the compounds where X is 0 and method B is used to prepare compounds where X is S.

METHOD A

1. The appropriate S-alkyl phosphonodithioic halide is reacted with a suitable alkoxide according to the equation:

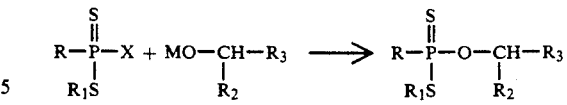

in which R-$R_3$ and n are as defined above, X stands for halogen, and M stands for an alkali metal, preferably sodium or potassium.

This reaction is carried out at a temperature of from about 0° to about 70° C., preferably from about 0° to 25° C. in an organic solvent. Suitable solvents include aromatic hydrocarbons such as benzene or toluene and ethers such as diethyl ether or tetrahydrofuran (the preferred solvent). The alkoxide is produced by a reaction of an appropriate alcohol with an alkali metal-containing base. Suitable bases include sodium and potassium hydride, with sodium hydride preferred. The desired product can be recovered and purified by evaporation of solvent and chromatography.

The S-alkyl phosphonodithioic halide may be prepared by any conventional means, such as by reaction of an alkyl mercaptan with an alkyl phosphonothioic dihalide as described in U.S. Pat. No. 4,258,038.

The alcohol may be prepared by conventional means, such as reaction of the corresponding N-oxide with acetic anhydride followed by hydrolysis as described in J. Am. Chem. Soc. Vol. 76, 1286 (1954).

METHOD B

This procedure involves a two-step process. In the first step the appropriate alkyl thionopnosphine sulfide is reacted with two equivalents of a mercapta- in the presence of a base to produce a thioic acid salt, according to the equation:

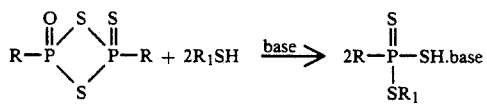

In the second step, the thioic acid salt is reacted with the appropriate halide:

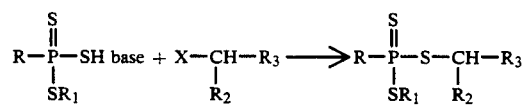

R, $R_1$, $R_2$, $R_3$ and n are as defined above and X stands for halogen.

The starting material sulfides may be obtained for instance by the procedure described in P. E. Newallis et al., Journal of Organic Chemistry, 1962, Vol. 27, p. 3829.

Step One is advantageously carried out at a temperature of from about—40° C. to about 150° C., preferably from about 0° to about 70° C., in an organic solvent in the presence of a base, preferably a tertiary amine. Suitable solvents include aromatic hydrocarbons such as benzene or toluene, ethers such as diethyl ether or tetrahydrofuran, and ketones such as acetone. Suitable tertiary amines include triethylamine, dimethylaniline, diethylaniline, and pyridine. Inorganic bases such as sodium hydroxide could be used in this step, but are less desirable as the resulting salts are less soluble in the solvents utilized. As the reaction is exothermic, the base is preferably added dropwise when operating on the laboratory scale. The product may be recovered by evaporating or distilling off the solvent.

Step Two is conducted in an organic solvent such as that utilized in the first reaction, at a temperature of from about 20° C. to about 130° C., preferably from about 20° to about 70° C. The halide may be either a chloride or bromide. The product may be recovered by removing the precipitated salt, followed by evaporating or distilling off the solvent, and purification by either chromatography or distillation.

The following represent examples of the preparation of compounds of this invention.

EXAMPLE 1

Preparation of S-t-butyl O-(pyrid-2-yl-1-ethyl) ethylphosphonodithioate (Compound 16 herein)

To a slurry of 0.22 grams (g) (0.0056 mole) of oil free sodium hydride in 10 ml of tetrahydrofuran under nitrogen and at room temperature was added 0.63 g (0.0051 mole) of α-(2-pyridyl)-ethanol. After the initial gas evolution ceased the reaction mixture was refluxed for five minutes and allowed to cool to room temperature. After cooling, 1.0 g (0.0046 mole) of S-t-butyl-ethylphosphonothioic chloride was added resulting in a gelatinous mixture. The mixture was combined with 60 ml of diethyl ether and washed with water and brine and dried with magnesium sulfate. Purification was effected by thin-layer (4mm, silica gel) chromatography, with 75:25 hexane-acetone as eluent. The isolated product yielded 1.07 g of clear, colorless, fairly mobile oil. The structure was confirmed by nuclear magnetic resonance, mass and infrared spectroscopy.

EXAMPLE 2

Preparation of S-t-butyl O-(4-chloropyrid-2-yl-methyl) ethylphosphonodithioate (Compound 7 herein)

To a slurry of 0.31 grams (g) (0.0077 mole) of oil-free sodium hydride in 7 millititers (ml) of anhydrous tetrahydrofuran maintained under nitrogen at room temperature was added 1.0 g (0.00 7 mole) of 4-chloro-2-hydroxymethylpyridine. The resultant mixture was refluxed for five minutes under nitrogen. After cooling, a blue green solution resulted to which 1.51 g (0.0069 mole) of S-t-butyl-ethylphosphonothioic chloride was added. After 45 minutes, 100 ml of diethyl ether was added. The solution was washed with 50 ml water and 50 ml brine and dried with magnesium sulfate. Evaporation afforded 2.03 g of clear, yellow mobile oil. Purification with a thin-layer chromatograph (4 mm silica get) with 90:10 hexaneacetone as eluent afforded 1.14 g theoretical yield of the title compound, a clear, nearly colorless oil. The structure was confirmed by nuclear magnetic resonance, mass and infrared spectroscopy.

The following Table I depicts representative compounds of this invention, which may be prepared by the process previously described. Structures of these compounds were confirmed by analysis as above.

TABLE I $$\begin{array}{c} R \diagdown \overset{S}{\underset{\|}{}} \\ \phantom{R}P-X-CH-R_3 \\ R_1S \diagup \phantom{P-X-C}R_2 \end{array}$$

| Cmpd. No. | X | R | $R_1$ | $R_2$ | $R_3$ | $R_4$ | $R_5$ |
|---|---|---|---|---|---|---|---|
| 1 | O | $CH_3$ | $t-C_4H_9$ | H | 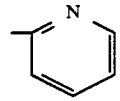 | H | — |
| 2 | O | $C_2H_5$ | $s-C_4H_9$ | H | 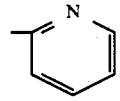 | H | — |
| 3 | O | $C_2H_5$ | $t-C_4H_9$ | H | 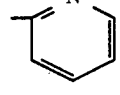 | 6-Cl | — |
| 4 | O | $C_2H_5$ | $t-C_4H_9$ | H | 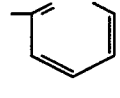 | H | — |
| 5 | S | $C_2H_5$ | $t-C_4H_9$ | H | 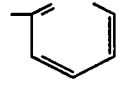 | H | — |
| 6 | O | $C_2H_5$ | $t-C_4H_5$ | H | 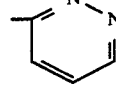 | H | — |

TABLE I-continued $$\begin{array}{c} R \quad S \\ \diagdown \parallel \\ P-X-CH-R_3 \\ \diagup \quad | \\ R_1S \quad R_2 \end{array}$$

| Cmpd. No. | X | R | $R_1$ | $R_2$ | $R_3$ | $R_4$ | $R_5$ |
|---|---|---|---|---|---|---|---|
| 7 | O | $C_2H_5$ | $t-C_4H_9$ | H | pyridyl | 4-Cl | — |
| 8 | O | $C_2H_5$ | $t-C_4H_9$ | H | pyridyl | 4-$CF_3$ | — |
| 9 | O | $C_2H_5$ | $t-C_4H_9$ | H | pyridyl | 5-$CH_3$ | — |
| 10 | O | $C_2H_5$ | $t-C_4H_9$ | H | pyridyl | 6-$CH_3$ | — |
| 11 | O | $C_2H_5$ | $t-C_4H_9$ | H | pyridyl | 3-$CH_3$ | — |
| 12 | O | $C_2H_5$ | $t-C_4H_9$ | H | pyridyl | 4,6-$CH_3$ | — |
| 13 | O | $C_2H_5$ | $t-C_4H_9$ | H | pyridyl | 4-Cl, 6-$CH_3$ | — |
| 14 | O | $C_2H_5$ | $t-C_4H_9$ | H | pyridyl | 4-$CH_3$ | — |
| 15 | O | $C_2H_5$ | $t-C_4H_9$ | H | pyridyl | 4-$CH_3$, 6-Cl | — |
| 16 | O | $C_2H_5$ | $t-C_4H_9$ | $CH_3$ | pyridyl | H | — |
| 17 | S | $C_2H_5$ | $s-C_4H_9$ | H | pyridyl | H | — |
| 18 | S | $C_2H_5$ | $s-C_4H_9$ | H | quinolyl | — | — |

TABLE I-continued
$$\underset{R_1S}{\overset{R}{\phantom{|}}}\underset{\phantom{|}}{\overset{S}{\underset{\|}{P}}}-X-\underset{R_2}{\overset{\phantom{|}}{C}H}-R_3$$
| Cmpd. No. | X | R | R₁ | R₂ | R₃ | R₄ | R₅ |
|---|---|---|---|---|---|---|---|
| 19 | S | CH₃ | s-C₄H₉ | H | 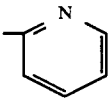 | H | — |
| 20 | O | C₂H₅ | t-C₄H₉ | H | 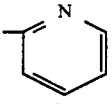 | 4-Br | — |
| 21 | O | C₂H₅ | t-C₄H₉ | H | 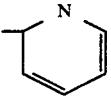 | 4-F | — |
| 22 | O | C₂H₅ | t-C₄H₉ | CN | 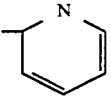 | H | — |
| 23 | O | C₂H₅ | t-C₄H₉ | H | 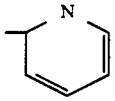 | 3,5,6-Cl | — |
| 24 | O | CH₃ | t-C₄H₉ | H | 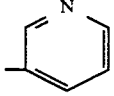 | H | — |
| 25 | O | C₂H₅ | s-C₄H₉ | H | 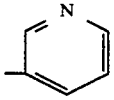 | H | — |
| 26 | O | CH₃ | t-C₄H₉ | H | 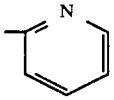 | H | — |
| 27 | O | C₂H₅ | s-C₄H₉ | H | 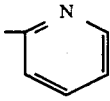 | H | — |
| 28 | O | CH₃ | t-C₄H₉ | H | 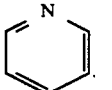 | H | — |
| 29 | O | C₂H₅ | s-C₄H₉ | H | 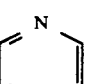 | H | — |
| 30 | O | C₂H₅ | t-C₄H₉ | H | 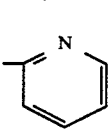 | 4-OCH₃ | — |

TABLE I-continued $$\begin{array}{c} R \quad S \\ \diagdown \| \\ P-X-CH-R_3 \\ \diagup \quad | \\ R_1S \quad R_2 \end{array}$$

| Cmpd. No. | X | R | $R_1$ | $R_2$ | $R_3$ | $R_4$ | $R_5$ |
|---|---|---|---|---|---|---|---|
| 31 | O | $C_2H_5$ | $t-C_4H_9$ | H | (pyridin-2-yl) | 4-$SCH_3$ | — |
| 32 | O | $C_2H_5$ | $t-C_4H_9$ | H | (pyrimidin-2-yl) | — | H |
| 33 | O | $C_2H_5$ | $t-C_4H_9$ | H | (pyrimidin-2-yl) | — | 4-$CH_3$ |
| 34 | O | $C_2H_5$ | $t-C_4H_9$ | H | (pyrimidin-2-yl) | — | 4-$CH_3$, 6-$CH(CH_3)_2$ |

INSECTICIDAL EVALUATION TEST

The compounds in Table I above were tested for insecticidal activity using the following testing procedures. LC-50 values, based on the results of these tests, and/or calculated according to dosage-mortality curves, are expressed in Table II.

Tobacco Budworm [*Heliothis virescens* (Fabricius)]

Cotton (Gossypium sp.) leaves were sprayed with the test compounds using a track sprayer at a volume of 10 gal/acre. Formulated materials were diluted in deionized water, and technical samples were diluted in 50:50 acetone:deionized water. One leaf was sprayed for each rate tested using a minimum of 5 rates per compound. Upon drying, the leaves were placed in petri dishes containing moistened filter paper. Five first-instar tobacco budworm larvae were transferred to cups. One cotton leaf was removed from the petri dish and placed treated surface down on one of the cups containing the larvae. A lid was then fitted on the cup, creating a leaf plug. A typical test consisted of 5 plugs per leaf. The cups were placed in a high humidity chamber for 72 hours at 80° F. Test concentrations ranged from 0.1% downward. The LC-50 values are expressed below in Table II under the heading "TBW" in terms of ppm of the test compound in the solution.

Cabbage Looper [(*Trichoplusia ni* (Hubner)]

Test compounds were diluted in a 50:50 acetone:water solution. Cotyledons of hyzini squash (*Calabacita abobrinha*), approximately 1 × 1.5 in., were immersed in the test solutions for 2-3 seconds and placed on a wire screen to dry. The dried leaves were placed in petri dishes containing a moistened piece of filter paper and infested with 5 second-instar looper larve. Mortality of the larvae was recorded 3 days later. Test concentrations ranged from 0.1% downward.

The LC-50 values are expressed below in Table II under the heading "CL" in terms of ppm of the test compound in this solution.

Black Bean Aphid [*Aphis fabae* (Scop.)]

Nasturtium plants (Tropaeolum sp.) approximately 5 cm tall, were transplanted into sandy loam soil in small cups and infested with 25-50 black bean aphids of mixed ages. Twenty-four hours later they were sprayed to the point of run-off with 50:50 acetone-water solutions of the test compounds. Treated plants were held in the greenhouse and mortality was recorded after 48 hours. Test concentrations ranged from 0.1% downward. The LC-50 values are expressed below in Table II under the heading "APH" in terms of ppm of the test compound in the sprayed solution.

Maize Weevil [*Sitophilos zeamais* (Motschulsky)]

Test compounds were diluted in a 50:50 acetone-water solution. Four corn seeds [Zea mays (L.)] were immersed in test solutions for 2-3 seconds and allowed to dry. The treated seeds were placed in 1 oz. plastic cups with 10 adult weevils. The cups were covered with plastic lids and kept in a controlled chamber at 25° C. Mortality was recorded 48 hours after treatment. Each treatment was replicated twice. Test concentrations ranged from 0.1% downward. The LC-50 valves are expressed below in Table II under the heading "MW" in terms of ppm of the test compound in the solution.

Acaricidal Evaluation Test

The two-spotted mite (SM) [*Tetranychus urticae* (Koch)] was employed in tests for miticides. The test procedure was as follows:

Pinto bean plants (Phaseolus sp.) approximately ten cm tall, were transplanted into sandy loam soil in eight oz waxed Dixie Cups and thoroughly infested with mites of mixed ages and sexes. Twenty-four hours later, the infested plants were inverted and dipped for two to three seconds in 50:50 acetone:water solutions of the test chemicals. Treated plants were held in the greenhouse, and five days later mortality was determined for both the adults and the nymphs hatching from eggs which were on the plants at the time of treatment. Mortality was also recorded. Test concentrations range from ten ppm downward. The LC-50 values are expressed below in Table II under the heading "SM" in terms of ppm of the test compound in the solution.

TABLE II

| Cmpd. No. | (LC-50 PPM) SPECIES/STAGE | | | | |
|---|---|---|---|---|---|
| | TBW/First | CL/Second | APH/All | MW/Adult | SM/Motile |
| 1 | 18 | 24 | 100 | 30 | 28 |
| 2 | 70 | 70 | 20 | — | 80 |
| 3 | 42 | 29 | 30 | 45 | 8 |
| 4 | 13 | 26 | 20 | 31 | 10 |
| 5 | 13 | 45 | 20 | 21 | — |
| 6 | — | >50 | 50 | 42 | — |
| 7 | 21 | 32 | 16 | 25 | 3 |
| 8 | 30 | 24 | 30 | 7 | 25 |
| 9 | 39 | >50 | 50 | 40 | 40 |
| 10 | 37 | >50 | 25 | 34 | 23 |
| 11 | 49 | 70 | 20 | 80 | 50 |
| 12 | >80 | 80 | 20 | >100 | 40 |
| 13 | 96 | 80 | 30 | 95 | 20 |
| 14 | >80 | 80 | 20 | 41 | 50 |
| 15 | >80 | >100 | >50 | 100 | 25 |
| 16 | — | 40 | 30 | — | >50 |
| 30 | >64 | >50 | — | >50 | 50 |
| 31 | 14 | >50 | — | 23 | 8 |

The insecticidal activity, and therefore the inclusion of a compound not mentioned specifically herein within the class of compounds of this invention, as determined by the general formula, may be determined by evaluating such a compound using one or more of the above-described procedures. If a test compound demonstrates activity against one or more of the insects mentioned, by virtue of causing 50 percent or greater mortality at the initial evaluation level, it is considered "insecticidal" for the purposes of this invention.

In practice, a pure compound can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein.

Solid carriers or diluents included in such compositions or formulations may include, for example, ground natural minerals such as kaolins, alumina, calcium carbonate, silica, kieselguhr, clays, etc; ground synthetic minerals such as various silicates and aluminosilicates and ground vegetable products such as bark, cornmeal, sawdust, cellulose powder and the like. Compositions containing sorptive clays will usually also contain a stabilizer, such as a glycol, to prevent or minimize degradation of the active ingredient.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of akali and alkaline earth meta salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1–50 microns in diameter, including the active compound and optionally a solvent. The encapsulating material is an inert porous membrane of a polymeric material.

Solid encapsulate compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 50 to 85% active compound; aqueous suspensions: 20 to 50% active compound; dusts and powders: 50 to 20% active compound; granules and pellets: 5 to 20% active compounds.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. The particular pesticide included in the mixture will depend upon its intended utility and the type of complementary action required. Examples of suitable insecticides include the following:

(a) natural pyrethrins or pyrethroids such as permethrin, fenvalerate, deltamethrin, cyhalothrin, biphenthrin, fenpropathrin, cyfluthrin, tefluthrin, empenthrin, ethofenprox, tetramethrin, bioallethrin, fenfluthrin, prallethrin, 5-benzyl- 3-furylmethyl-(E)-(1R,3S)-2,2-dimethyl-3-(2-oxothiolan-3-ylidene-methyl)cyclopropane carboxylate, and pentafluorobenzyl (cis)-3-[2-fluoro-2-(methoxycarbonyl)-ethenyl]-2,2-dimethylcyclopropane carboxylate;

(b) other organophosphates such as profenofos, sulprofos, phosmet, dichlorvos, methyl parathion, azinphosmethyl, dimeton-s-methyl, heptenophos, thiometon, fenamiphos, monocrotophos, triazophos, methamidophos, dimethoate, phosphamidon, malathion, chlorpyrifos, phosalone, fensulfothion, fonofos, phorate, phoxim pyrimiphosmethyl, fenitrothion and diazion;

(c) carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) benzoyl ureas such as triflumuron and chlorofluazuron;

(e) organic tin compounds such as cyhexatin, fenbutatin oxide, and azocyclotin;

(f) macrolides such as avermectins or milbemycins, such as abamectin, avermectin, and milbemycin;

(g) hormones and synthetic mimics thereof such as juvenile hormone, juvabione, ecdysones, methoprene and hydroprene;

(h) pheromones; and (i) organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stem borerspecific insecticides for use in rice such as cartap or buprofesin, can be employed. Alternatively, insecticides specific for particular insect species/stages, for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylon, cyromazine, methoprene, chlorfluazuron and diflubenzuron may also be included in the compositions. Such compositions may also contain soil disinfectants or fumigants and may further contain fertilizers, thus making it possible to provide multipurpose compositions containing one or rore of the active compounds described herein as well as, optionally, other pesticides and also fertilizers, all intended and formulated for use as the same locus.

Active compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 112 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compounds of this invention could be used to control a variety of insects such as:

*Myzus persicae* (aphid)
*Aphis gossypii* (aphid)
*Aphis fabae* (aphid)
*Megoura viceae* (aphid)
*Aedes aegypti* (mosquito)
Anopheles spp. (mosquitos)
Culex spp. (mosquitos)
Dysdercus fasciatus (capsid)
*Musca domestica* (housefly)
*Pieris brassicae* (white butterfly)
*Plutella maculipennis* (diamond back moth)
*Phaedon cochlaeriae* (mustard beetle)
Aonidiella spp. (scale insects)
Trialeuroides spp. (white flies)
*Bemisia tabaci* (white fly)
*Blattella germanica* (cockroach)
*Periplaneta americana* (cockroach)
*Blatta orientalis* (cockroach)
*Spodoptera littoralis* (cotton leafworm)
*Heliothios virescens* (tobacco budworm)
*Chortiocetes terminifera* (locust)
Diabrotica spp. (rootworms)
Agrotis spp. (cutworms)
*Chilo suppressalis* (stem borer)
*Chilo partellus* (maize stem borer)
*Nilaparvata lugens* (planthopper)
*Nephottex virescens* (leafhopper)
*Nephotettix cincticeps* (leafhopper)
*Panonychus ulmi* (European red mite)
*Panonychus citri* (citrus red mite)

*Tetranychus urticae* (two-spotted spider mite)
*Tetranychus cinnabarinus* (carmine spider mite)
*Phyllcoptruta oleivora* (citrus rust mite)
*Polyphagotarsonemus latus* (broad mite)
Brevipalpus spp. (mites)

Composition containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of powder dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | Weight % |
|---|---|
| Composition A: Wettable Powder | |
| Compound 1 | 80 |
| wetting agent (sodium dialkyl-naphthalene sulfonate) | 1 |
| dispersing agent (sodium lignosulfonate | 4 |
| diluent (aluminum magnesium silicate) | 15 |
| Total | 100% |
| Composition B: Granular Solid | |
| Compound 2 | 10 |
| calcined diatomaceous earth granules or attapulgite clay granules | 85 |
| triethylene glycol | 5 |
| Total | 100% |
| Composition C: Dilute Solution | |
| Compound 1 | 5 |
| solvent (xylene) | 95 |
| Total | 100% |
| Composition D: Emulsifiable Concentrate | |
| Compound 2 | 50 |
| Emulsifier (blend of metal sulfonates and polyoxyethylene ethers) | 10 |
| solvent (xylene) | 40 |
| Total | 100% |
| Composition E: Concentrated Solution | |
| Compound 1 | 90 |
| solvent (xylene) | 10 |
| Total | 100% |

We claim:
1. A compound having the formula

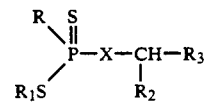

in which
R is $C_1-C_3$ alkyl;
$R_1$ is $C_4-C_6$ branched alkyl;
$R_2$ is hydrogen, methyl, ethyl, or $C_2-C_4$ alkynyl;
$R_3$ is $R_3$ is 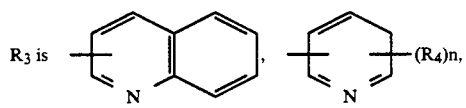

$R_4$ is halo, $C_1-C_2$ haloalkyl, $C_1-C_4$ alkoxy, $C_1-C_4$ thioalkyl or mono- or di- $C_1-C_2$ alkylamino;
n is 1-3; and
X is O or S.
2. A compound according to claim 1 in which X is O.
3. A compound according to claim 1 in which X is S.
4. A compound according to claim 1 in which $R_1$ is tertiary butyl.
5. A compound according to claim 1 in which R is methyl or ethyl.
6. A compound according to claim 1 in which $R_2$ is hydrogen.
7. A compound according to claim 2 in which $R_4$ is 4-chloro.
8. A compound according to claim 2 in which $R_4$ is 6-chloro.
9. A compound according to claim 2 in which $R_4$ is 4-trifluoromethyl.
10. A compound according to claim 2 in which $R_4$ is 4-chloro, 6-methyl.
11. A compound according to claim 2 in which $R_4$ is 4-methyl, 6-chloro.
12. A compound according to claim 2 in which $R_4$ is 4-bromo.
13. A compound according to claim 2 in which $R_4$ is 4-fluoro.
14. A compound according to claim 2 in which $R_4$ is 4,5,6 trichloro.
15. An insecticidal composition comprising:
(a) an insecticidally effective amount of a compound having the formula

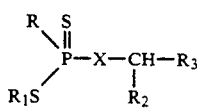

in which
R is $C_1$-$C_3$ alkyl;
$R_1$ is $C_4$-$C_6$ branched alkyl;
$R_2$ is hydrogen, methyl, ethyl, or $C_2$-$C_4$ alkynyl;
$R_3$ is

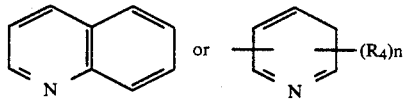

$R_4$ is halo, $C_1$-$C_2$ haloalkyl, $C_1$-$C_4$ alkoxy, $C_1$-$C_4$ thioalkyl or mono- or di- $C_1$-$C_2$ alkylamino;
n is 1-3;
X is O or S; and
(b) an insecticidally suitable inert diluent or carrier.

16. A method for inhibiting or controlling insects comprising applying to an insect, the locus of an insect, or a locus at which insecticidal control is desired, an insecticidally effective amount of a compound having the formula

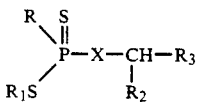

in which
R is $C_1$-$C_3$ alkyl;
$R_1$ is $C_4$-$C_6$ branched alkyl;
$R_2$ is hydrogen, methyl, ethyl, or $C_2$-$C_4$ alkynyl;
$R_3$

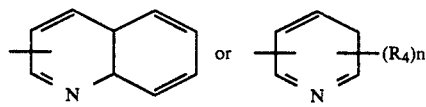

$R_4$ is halo, $C_1$-$C_4$ alkyl, $C_1$-$C_2$haloalkyl, $C_1$-$C_4$ alkoxy, $C_1$-$C_4$ thioalkyl or mono- or di- $C_1$-$C_1$ alkylamino;
n is 1-3;
X is O or S.

17. A method according to claim 16 in which the insect to be inhibited or controlled is a Lepidoptera insect.

18. A compound having the formula

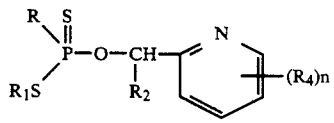

in which
R is ethyl or methyl;
$R_1$ is t-butyl;
$R_2$ is H or methyl;
$R_4$ is independently selected from the group halogen, haloalkyl, methoxy or thiomethyl.

* * * * *